United States Patent [19]

Katz

[11] Patent Number: 4,528,689

[45] Date of Patent: Jul. 9, 1985

[54] SOUND MONITORING APPARATUS

[75] Inventor: Hart V. Katz, Willowdale, Canada

[73] Assignee: International Acoustics Incorporated, Palatine, Ill.

[21] Appl. No.: 558,746

[22] Filed: Dec. 7, 1983

Related U.S. Application Data

[63] Continuation-in-part of Ser. No. 304,607, Sep. 22, 1981.

[51] Int. Cl.³ .................. H04R 23/00; A61B 5/02
[52] U.S. Cl. .................... 381/67; 128/715; 360/32; 381/31; 381/32; 381/34; 381/38; 381/56
[58] Field of Search ............. 381/67, 56, 31, 32, 381/68, 34, 38; 179/107 R; 360/8, 32; 128/715

[56] References Cited

U.S. PATENT DOCUMENTS

| 3,030,946 | 4/1962 | Richards | 381/67 |
|---|---|---|---|
| 3,104,284 | 9/1963 | French et al. | 381/34 |
| 3,160,708 | 12/1964 | Andries et al. | 381/67 |
| 3,789,144 | 1/1974 | Doyle | 381/32 |
| 3,846,585 | 11/1974 | Slosberg et al. | 381/67 |
| 3,895,316 | 7/1975 | Fein | 455/109 |
| 4,048,444 | 9/1977 | Giampapa | 381/67 |
| 4,071,694 | 1/1978 | Pfeiffer | 381/67 |
| 4,072,822 | 2/1978 | Yamada | 381/67 |
| 4,424,815 | 1/1984 | Kuntz | 128/715 |

OTHER PUBLICATIONS

Fairbanks et al., "Time or Frequency Compression-Expansion of Speech" Reprinted from Transcripts of National Convention of I.R.E.-Professional Group on Audio AU2-No. 1, 1954.

Francis F. Lee, "Time Compression and Expansion of Speech by Sampling Method" *Journal of Audio Engineering Society*, vol. 20, No. 9, Nov. 1972, pp. 738-742.

Primary Examiner—Gene Z. Rubinson
Assistant Examiner—Danita R. Byrd
Attorney, Agent, or Firm—Dennison, Meserole, Pollack & Scheiner

[57] ABSTRACT

Sound monitoring apparatus is described which provides a slowed down version of the original sound, e.g. a heart beat without changing the quality of the sound as perceived by a trained listener such as a physician. The amount by which the sound is slowed down can be varied by the user. The original sound is converted to an analog electrical signal, digitized and electronically processed in a microprocessor-based circuit such that digital data corresponding to cycles of the analog signal are stored in a random access memory. The microprocessor reads out the digital data a predetermined number of times corresponding to a number of sound cycles according to the rate set by the physician. The digital data is reconstituted into sound which is composed of replicated sets of cycles of the original sound. The repetition rate of the heart-beat in the output sound is a fraction of the repetition of the heart-beat in the original sound but the sound quality appears the same to the physician as the pitch is invariant. In a preferred embodiment stored digital data corresponding to each input half signal is duplicated and data corresponding to the duplicated positive half-cycle is inverted to give data corresponding to a negative half-cycle and the non-duplicated negative half-cycle data is inverted to give a positive half-cycle data. In another embodiment, the signal processing circuitry is incorporated into a conventional stethoscope and the circuitry is implemented using low power CMOS technology. The invention has application in other fields such as vibration analysis.

25 Claims, 9 Drawing Figures

SOUND MONITORING APPARATUS

This application is a Continuation-In-Part of U.S. patent application Ser. No. 304,607, filed 22nd Sept., 1981 to Hart V. Katz.

The present invention relates to sound monitoring apparatus. In particular the invention relates to electronic stethoscopes for use by physicians, and especially to those suitable for use in cardiology.

Sound monitoring, or auscultation, is an important aspect in the evaluation of the physical condition of an individual, and is particularly important in the diagnosis of certain pathological conditions which are manifested by abnormal sounds. The bifurcated stethoscope with binaural earpieces and a bell or diaphragm for receiving sound is probably the standard stethoscope and is widely used by physicians to assist in the analysis and interpretation of physiological sounds. This stethoscope is generally satisfactory and reliable but its simplicity is also a significant disadvantage as many physiological sounds are reproduced without sufficient clarity to permit rapid and accurate diagnosis of the physiological precursor of the sound.

Consequently, electronic stethoscopes have been proposed to modify the physiological signal to produce an audible signal which has clarity and which more accurately reflects the original physiological sound, facilitating analysis and diagnosis by the physician. One such prior proposal involved inserting a microphone within the bell, amplifying the acoustic signal detected by the microphone and using loudspeakers to present an audible signal from ear pieces of the stethoscope. This electronic stethoscope was unsatisfactory and did not accurately reproduce the original physiological sound. For example, while monitoring heart sounds it was found that the resulting sound was considerably louder than the sound normally heard using a conventional stethoscope and "sound" itself differed so much in quality, i.e. tone and pitch, that physicians trained to recognise the sounds of the conventional stethoscope, had considerable difficulty in interpreting these sounds and relating them to the physiological phenomena. Thus, diagnosis was long, difficult and often inaccurate and for these reasons such electronic stethoscopes were not well accepted by physicians.

U.S. Pat. No. 3,562,428 relates to an electronic stethoscope which modulates the detected frequency range, to a frequency range more easily heard but this again caused the quality of the sound to differ substantially from the usual sounds heard by the physician and as such this device is not in common use.

U.S. Pat. Nos. 3,247,324, 3,311,703 and 3,396,241 relates to electronic stethoscopes with filters for removing certain parts of the frequency spectrum of the physiological sound detected. This filtering is a significant disadvantage since the physician is used to interpreting the whole acoustic signal and the resulting filtered signals differed so much in amplitude and quality, tone and pitch that analysis and diagnosis was difficult and often inaccurate.

U.S. Pat. No. 3,846,585 discloses a recording stethoscope, the primary intention of which is to faithfully record the same sound as is heard by the physician for future analysis. The recorded signal can be played back through the stethoscope to simulate the original sound. This is achieved by splicing the single conduit to the bell and inserting a T-piece which is connected to an auxilliary conduit. Sound is diverted to a piezoelectric transducer in the auxiliary conduit which converts the sound waves into electrical signals which are recorded on tape. Apart from the insertion of the T-piece this is simply a conventional stethoscope and no electronic processing of the signal is performed before it is heard by the physician. This stethoscope has the same disadvantages as a conventional bell stethoscope.

U.S. Pat. No. 4,220,160 is directed to a device for transposing heart sounds into a frequency range detectable by the ear by converting the heart sounds into electrical signals with predetermined frequency components, processing these frequency components to give an output signal which consists of the sum and the difference between these frequency components, filtering the output signal to remove the difference between the frequency components and, from the sum of the frequency components, generating an output signal. This complex procesing of the original sound signal completely alters the subjective heart sound characteristics as heard by a physician and application of this system to a stethoscope would merely result in difficult and inaccurate diagnosis.

A further disadvantage of these prior art electronic stethoscopes is their sensitivity to interference from radio frequency (r.f.) signal sources. In a typical clinical environment this interference is not uncommon, and again results in poor clarity, difficult interpretation and diagnosis by the physician.

Such prior art electronic stethoscopes and conventional mechanical stethoscopes reproduce to the physician the physiological sound at the same rate as it is produced. Consequently, when investigating heart sounds, irregularities in the heart beat are frequently difficult to interpret by physcians as the irregularities occur too fast, for example in various forms of tachycardia.

One solution to this problem was to try to slow the sound rate down electronically by decreasing the frequency of the sound. However, this resulted in substantial variations in the pitch of the sound as heard by the physicians and they considered these "slowed sounds" quite unrelated to the original sound. Consequently, accurate interpretation and diagnosis of the physiological condition responsible for the sounds was virtually impossible.

It is an object of the present invention to obviate or mitigate the abovesaid disadvantages.

It is a still further object of the present invention to produce audible reproduction of a heart beat in which the pitch does not otherwise differ substantially to a listener from the pitch of a heart beat as heard through a conventional mechanical stethoscope.

The above-mentioned problems in the art are overcome by incorporating electronic signal processing means in a stethoscope which splits a cyclically varying sound signal into a number of individual cycles, repeats each individual cycle to form a set of cycles, successively reads out each set of cycles in the form of an analog output signal, converts the output signal to sound and presents this information acoustically to the physician.

In a preferred embodiment stored digital data corresponding to each input half cycle is duplicated and data corresponding to the duplicated positive half-cycle is inverted to give data corresponding to a negative half-cycle. The non-duplicated negative half-cycle data is inverted to give a positive half-cycle data. As the ear is insensitive to phase, the acoustic signal perceived by the physician, has the same pitch, tone and quality as an original sound but is effectively a slowed-down version of the original signal. The clarity and the quality of the reproduced signal is subjectively interpreted as being the same as the original. This is considered to be due to the close temporal repetition of the original cycles in each set and because the period between respective, successive repeated cycles of a set is such that the physician does not discriminate between the sound caused by each cycle of the set. The set of repetitive cycles is perceived as a single sound by the physician. Moreover, the repetitive cycles are perceived as physiological sounds familiar to the physician so that a rapid and accurate diagnosis of the physiological condition responsible for the sound can be achieved.

Further features, objects and advantages of the present invention will appear in the following description of embodiments of the invention which are described by way of example only with reference to the accompanying drawings, in which:

FIG. 1 diagrammatically illustrates a stethoscope incorporating signal processing apparatus;

Figure 1:
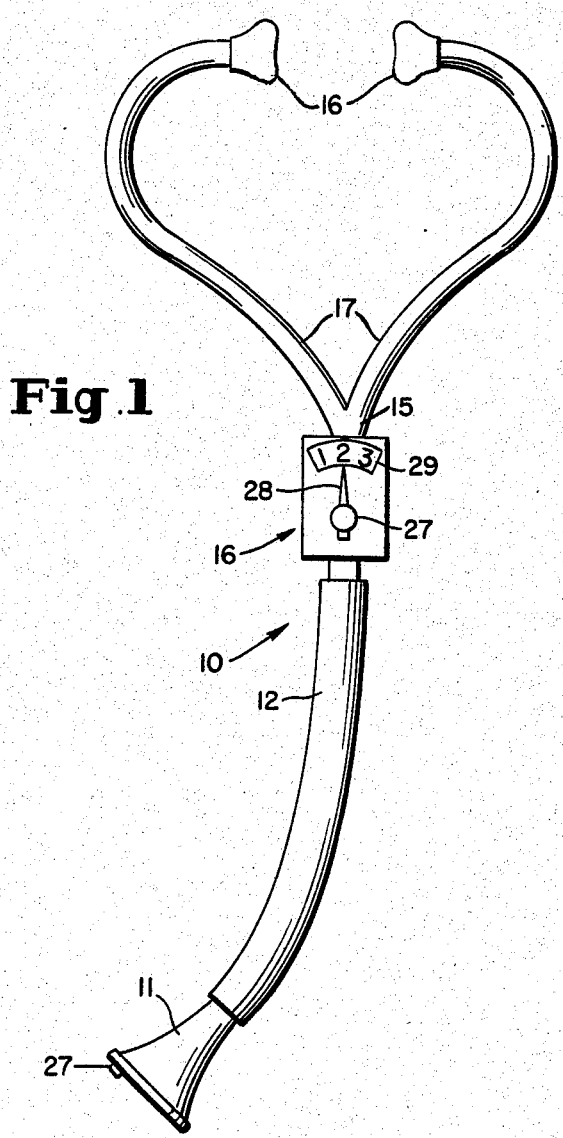
Figure 4:
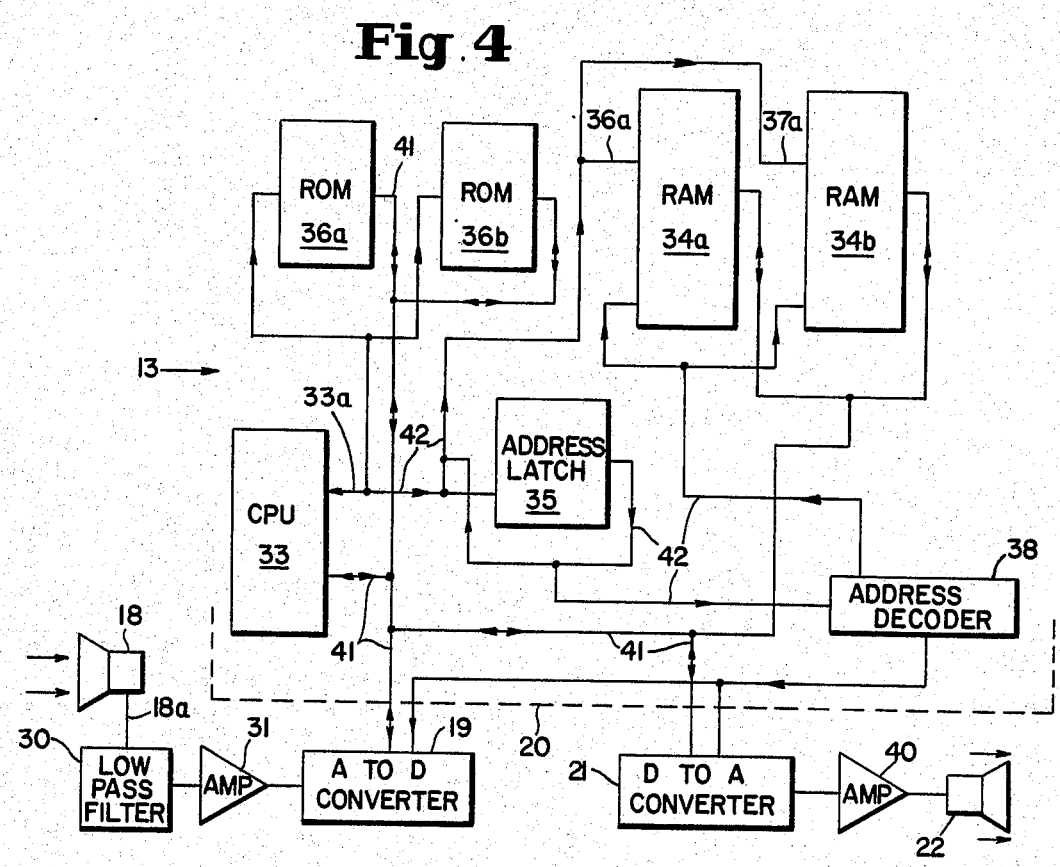
FIG. 4 is a more detailed block diagram of the electronic circuitry shown in FIG. 2.

Referring now in detail to FIG. 1 of the drawing, an electronic stethoscope, indicated generally by reference numeral 10, comprises a bell 11, connected by a flexible rubber tube 12 to a housing, indicated generally by reference numeral 14, which contains signal processing circuitry 13, the electronic components of the stethoscope to be described in more detail below. The housing 14 is connected to a second tube portion 15 which is bifurcated and each tube leg 17 is connected to an earpiece 16. The bell 11 has a microphone 18 at its lower end, which is connected to the circuitry 13 in the housing 14 (FIGS. 2, 4).

Figure 2:
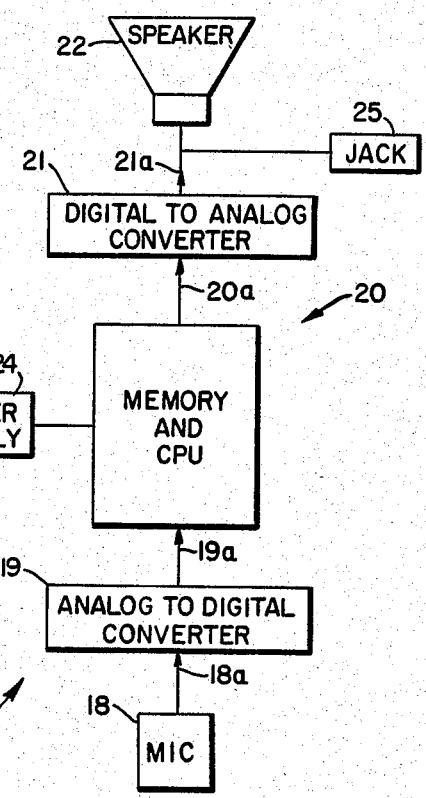
FIG. 2 is a block diagram of an electronic circuit used to process sound signals.

Referring now to FIG. 2 the microphone 18, has an output 18a connected to an analog-to-digital (A/D) converter 19, the output 19a of which is connected to a memory and central processing unit indicated generally by reference numeral 20, where the digitised analog input signal is stored and processed as described in greater detail hereinafter.

The memory and processing unit 20 has an output 20a which is connected to a digital to analog (D/A) converter 21. The output 21a of D/A converter 21 is connected to a loudspeaker 22 and to a recording jack 25. In use, the loudspeaker 22 emits an audible signal, which is transmitted through the bifurcated tube 15 into the earpieces 16. The housing 14 also contains a power supply 24, which is used to power all appropriate components. A rate select button 27 is provided on the housing 14 and the button 27 has a pointer 28 connected thereto, and adapted to be moved relative to a scale 29. The rate select button 27 is connected directly to the central processing unit 20. This rate select button 27 and scale 29 enable the physician to modify the processing of the sound signal by the electronic circuitry as will be described in more detail later.

In use, as will be appreciated, the physician locates the bell 11 on the surface of the body over the location at which the physiological sound, in this case a heart sound, is produced. He then listens to the heart sound by the earpieces 16. The sound which he listens to is obtained as follows with reference to FIGS. 3a and 3b of the drawings.

Figure 3A:
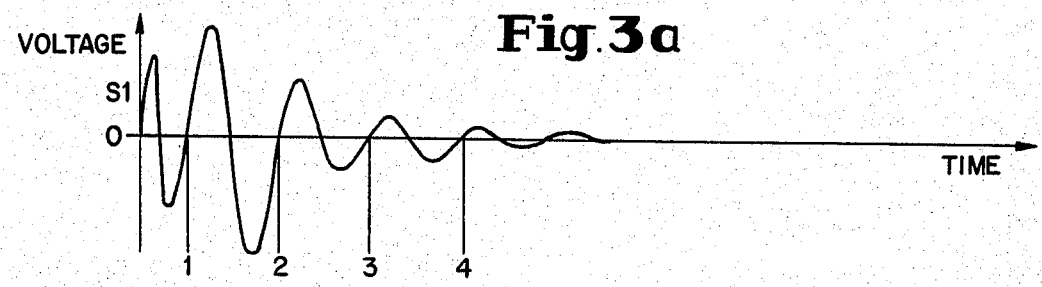
FIG. 3a is a waveform of an electrical signal representing a heart sound.

In FIG. 3a, a time varying electrical signal representative of a heart sound, S1, is provided at the output 18a of the microphone 18 in response to the heart sound impinging on the microphone 18. This heart sound is generally called the "lub" sound. It will also be appreciated by those skilled in the art that the 'lub' sound is always followed after a predetermined time by a 'dup' sound although the waveform corresponding to this sound is not shown in FIG. 3a. The time varying electrical signal, S1, which is a voltage versus time waveform is cyclic, and alternates between positive and negative values about a zero line. The first cycle of the waveform is completed at the zero crossing indicated by reference numeral 1, the second cycle is completed at the zero crossing, indicated by reference numeral 2, the third cycle is completed at the zero crossing represented by reference numeral 3, and so on.

Figure 3B:
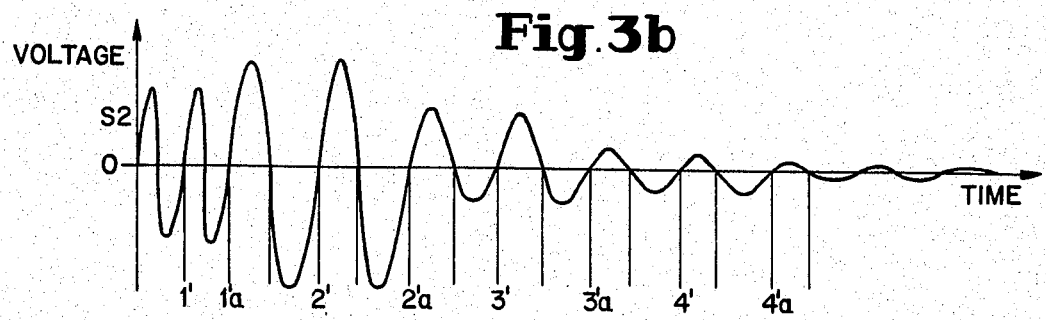
FIG. 3b is a waveform of an electrical signal of FIG. 3a representing the heart sound after it has been processed by the circuit of FIG. 2.

FIG. 3b shows a time varying electrical signal, S2, at the output 21a of the D/A converter 21, which corresponds to the analog input signal S1 after being electronically processed by the circuitry 13 shown in FIGS. 2, 4, as will be described in more detail later. Upon inspection of signal S2 and comparing it with the signal S1, the first cycle of the signal S2 is completed at the zero crossing 1', thus corresponding exactly in time to the first cycle of the signal S1. The next cycle of signal S2 is a repeat of its first cycle, this repeat being completed at the zero crossing 1'a. The next cycle (third) of the signal S2, corresponds to the second cycle of the signal S1, and is completed at the zero crossing 2' and is then immediately repeated, the repeat being completed at the zero crossing 2'a, etc. This procedure is repeated for the 'dup' sound, and so on for each heart beat.

When the signal $S_2$ is in audible form the heart sound is perceived by the physician as a slowed-down version of the original heart sound, as the physician hears the same tone and pitch as produced by the original heart sound, only slower. This is true in a technical sense as the same amount of information in a single cycle is still present in double cycles since the cycle period is effectively doubled.

Referring back to FIG. 1, when the pointer 28 is towards the number 2 on the scale 29, this represents an audible output which corresponds to one-half the rate of the original input sound signal, i.e. double cycle reproduction, and when the pointer points towards number 3 on the scale 29 this corresponds to an audible output of one-third of the rate of the original input sound signal, i.e. triple cycle reproduction.

The physician can also adjust the scale pointer so that the output sound is the same rate as the input sound, this is represented by the number 1 on the scale 29.

A more detailed description of the circuitry shown in FIG. 2 will now be given with reference to FIGS. 3 and 4. The microphone 18a has an output 18a which is filtered to around 250-300 Hz by a low pass filter 30 to produce a filtered signal. The filtered signal is then amplified by amplifier 31 and the amplified signal is passed to an analog to digital converter 19. The memory and central processing unit 20 are connected to the A/D converter 19 and to the D/A converter 21 by address and data buses, the data bus having double arrows in normal convention as will be appreciated by anyone skilled in the art. As illustrated, the central memory and processing unit 20 is made up of various components which are also interconnected to each other by the same data and address buses, as will also be appreciated by a man skilled in the art.

The amplified analog signal is sampled in the A/D converter 19 at a frequency of 1.5 KHz to provide corresponding digital signals of 8 bits. The digital data travels along the data bus 41 and is read by a central processing unit or microprocessor 33 which then generates addresses via the address latch 35 and stores the digital signals in the appropriate addresses in the random access memories (RAM's) 34a, 34b in accordance with a program stored in the read-only-memories (ROM's) 36a, 36b.

The output of the address latch 35 is connected via the address bus 42 to the CPU 33, the RAM'S 34a, 34b and to an address decoder 38. The output of the RAMS 34a, 34b is connected via the data bus 41 to the CPU 33 and to the D/A converter 21. The address decoder 38 decodes the address and ensures that the proper digital data is sent from the RAM'S to the CPU 33. The address decoder 38 is also connected via the address bus 42 to the A/D converter 19 and to the D/A converter 21.

Data is read into the RAMS 34a, 34b by the CPU 33 until the RAM is full, and then no more data is read in. The digital data is then read out of the RAM'S via the data bus 41 to the CPU 33 under control of the program in the ROM's 36a, 36b. It will be appreciated that when data is read out from the RAM's, the same data is retained in the respective memory addresses. The CPU 33 then checks the data and transmits it back along the data bus 41 to the D/A converter 21 where it is converted back into an analog voltage signal S2 as shown in FIG. 3b.

When the data is being read out, the CPU 33 checks each digital value and when it notes the digital value nearest the zero crossing the corresponding address of the digital value location is recorded in RAM's 34a, 34b. Data continues to be read-out until two-more zero-crossings are identified in the same way. The program then recognises that it has identified the limits of one full sound cycle. This causes the program to read out data in the same order from the RAM's 34a, 34b starting from the address of the original zero crossing obtained for that cycle. Thus, data corresponding to one cycle of the analog output cycle is read out twice. When this occurs for the switch 27 at position 2, the CPU advances to the next cycle of the original data in that it reads out the digital data and again counts the zero crossings until digital data corresponding to the next cycle is read out twice. This is repeated for all data.

This is repeated for the data stored in the RAMS's 34a, 34b. The digital signals are sent from the CPU 33 on the data bus 41 to the D/A converter 21 where they are converted back into analog electrial signals. As soon as the data in the RAM is being read out more data is entered into the RAM by the CPU 33.

The digital signals read out are converted back into analog electrical signals by the D/A converter 21 and thus the signal is amplified in the amplifier 40 and passed to the loudspeaker 22 which converts this signal (S2) back into sound. The sound wave then passes through conduits 17 and earpieces 16 to be heard by the trained ear of the physician.

As mentioned before the physician perceives the 'lub' sound composed of duplicate cycles as the same as the original sound. This is also true for the 'dup' sound. Therefore, the average time between successive overall cycles and hence the time between successive 'lub dup' sounds i.e. heart 'beats' is doubled. This is perceived by the physician as slowing down the rate of the heart beat by a factor of two. The quality of the sound and pitch appears unchanged to the physician and therefore clearly recognisable, facilitating interpretation and diagnosis of the physiological precursor of the heart beat.

It will be appreciated that the switch 27, connected to the CPU 33, (although not shown in the interest of clarity) may be positioned at scale location 1, 2 or 3 in which case digital data stored in the RAM for one cycle will only be read out the number of times shown on the scale. That is, in position 2 the digital data is read out twice corresponding to the original sound being slowed down by a factor of 2, and likewise position 3 provides a slow-down factor of 3.

Figure 5:
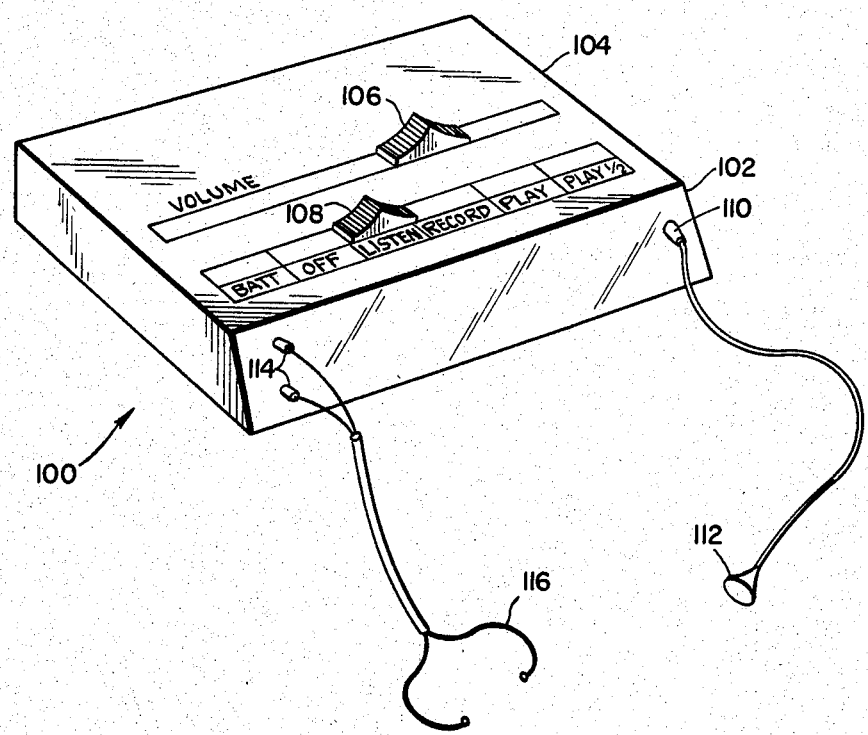
FIG. 5 is a diagrammatic representation of a preferred embodiment of a sound monitor.

Referring now to FIG. 5 a heart sound analyser, generally indicated by reference numeral 100 comprises a housing 102 having a top panel 104 on which two slider switches 106, 108 are located. Switch 106 is a volume control and switch 108 is a mode selection switch. The front panel 104 also has an input socket 110 to receive input sound signals from a microphone 112 and output sockets 114 to which a loudspeaker or headphones 116 may be connected. Rechargeable nickel cadmium batteries (not shown) provide power to the analyser.

The selector switch 108 is normally located in an off position and is movable between a number of modes, the mode selected being indicated by a light. Movement of the switch to the left gives a battery test mode; the switch is spring loaded in this direction so that it does not stay at battery test. The various switch modes to the right are listen, record, play and play ½.

In the listen mode the input sound signal is converted to a digital signal and then back to an analogue signal; it does not go to memory and is not processed in any other way. In the record mode, the input sound signal is recorded by sampling the signal at 2 kHz for six seconds. There is no sound output from the analyser when in the record mode.

The next position is play. In the play mode the data which is stored in the memory is replayed at normal speed; the data stored in the memory is converted back to an analogue signal and replayed. This mode is useful for recording sounds for subsequent analysis and comparisons, e.g., to investigate the effect of therapy over a prolonged period.

In the play ½ mode the sound is replayed at one-half frequency of the input sound signal. However, the signal is processed in a preferred manner to that described in the earlier embodiment. Instead of reading out each positive stored input cycle twice, the first half cycle of each stored cycle is read out, then the first half cycle is reversed and again read out. The negative cycle is read out inverted to give a positive cycle then is again read out normally to give the negative, cycle. This process is then repeated for the next and subsequent half-cycles, and will be described in greater detail later with reference to FIGS. 6 to 8.

Figure 6:
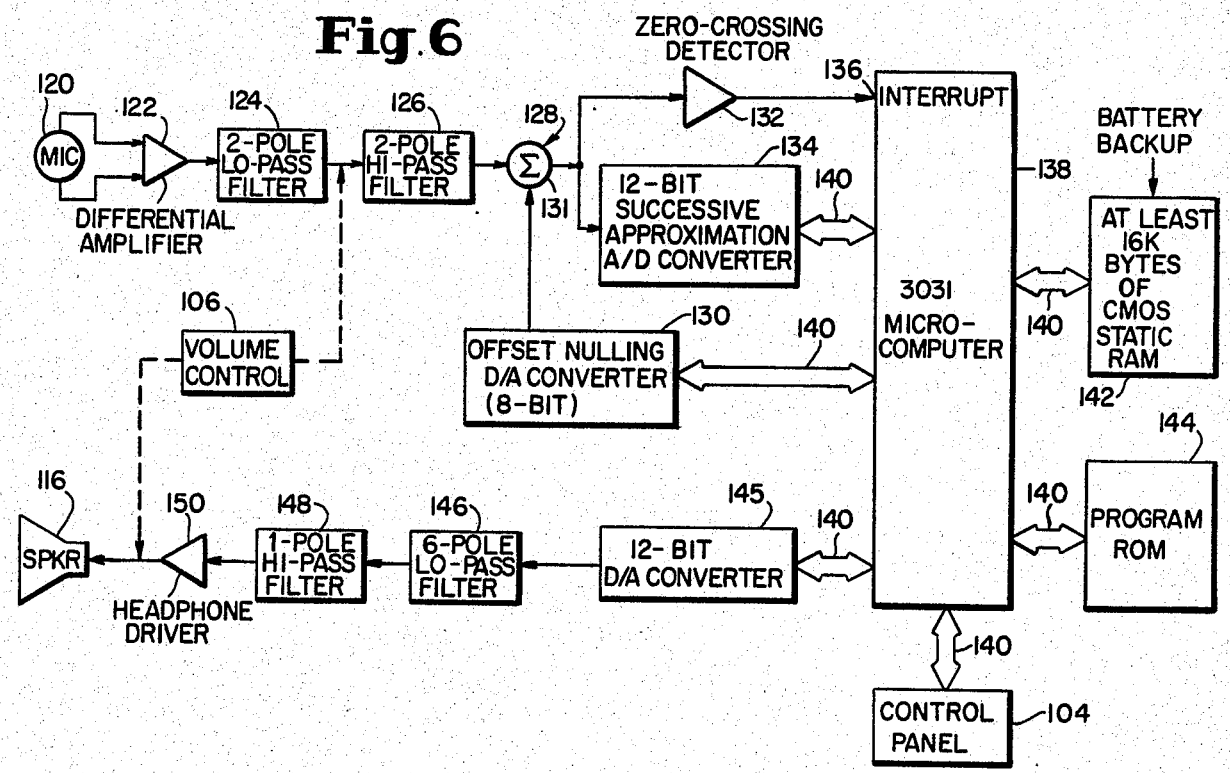
FIG. 6 is a block diagram of the electronic circuitry used in the monitor of FIG. 5.

Turning now to FIG. 6 which is a block diagram of the circuitry used in the monitor shown in FIG. 5, a microphone 120 for recording sound signals has its output connected to the inputs of a differential amplifier 122. The amplifier output is first passed through a low-pass filter 124 set at 600 Hz and then passed through an anti-rumble high pass filter 126 set at 50 Hz. The output of the filter 126 is connected at a summation node 128 with the output from an 8-bit offset nulling converter 130. The output 131 of the summation node is connected to a zero-crossing detector 132 and to a 12-bit successive approximeter analogue to digital (A/D) converter 134. The output of the zero-crossing detector 132 is connected to an interrupt input 136 in a 3031 microcomputer 138. The microcomputer contains, as will be appreciated by a person skilled in the art address latches and address decoders which are not shown in FIG. 6 in the interest of clarity. The output of the A/D converter 134 is connected to the microcomputer 138 via a data bus 140. The microcomputer 138 is connected by the data bus 140 to a 16 kilobyte CMOS (complementary metal oxide semiconductor) static RAM 142, to a programmable ROM 144, to the offset nulling D/A converter 130, and to the control panel 104. On the block diagram it appears that the microcomputer 138 is also connected to a separate D/A converter 145 by the data bus 140. However this D/A converter 145 is the A/D converter 134 used in reverse, but accessed at different times and therefore is shown separately in the interest of clarity. The output of the D/A converter 134 in the D/A mode is connected to a 6-pole low pass filter 146 set at 600 Hz. The filter 146 has a very sharp cut-off to remove the 'graininess of quantisation' because the ear is most sensitive around the sampling frequency and the output of the filter 146 is connected to a 1-pole hi-pass filter 148 which has a 50 Hz cut-off frequency. The low pass filter 148 output is converted via a headphone driver amplifier 150 to a headphone speaker 116. The volume control switch 106 is connected to the output of the low-pass filter 124 and the input of the driver adapter 150.

In use, when the selector switch 104 is in the listen mode, the sound is digitized by the A/D converter 134, and the digital signal immediately passed back through the D/A converter 135 under control of the microcomputer 138 to the loudspeaker 116. There is no other processing or storage of the digital data when the switch is in this mode.

When the selector switch 108 in the control panel 104 is in the record mode, the input sound signal is filtered, its baseline value being constantly adjusted to zero by the 8-bit D/A nulling offset to minimize drift and keep the signal substantially constant. The signal is sampled by the D/A converter at a frequency of 2 kHz for a period of 6 seconds and the digital data stored in the CMOS static RAM 142 by the microcomputer 138. This stored digital data is not read out in the record mode, and in this mode it could be transferred into another copy medium such as tape or disk for archiving.

When the selector switch 108 is moved to play position any stored data in the RAM 142 is read out, and converted to an analog signal which is a replica of the input signal. Additional input sound signals are digitised, stored in memory and then read out again, thus the physician hears a processed normal speed sound. There is no other processing of the data in this mode.

If the physician desires to examine the sound in greater detail the selector switch is moved to the play ½ mode, and in this mode the signal processing is very different. After the input signal has been filtered, its drift controlled and it has been digitized and stored in the RAM 142 the microcomputer executes an algorithm stored in the ROM 144 which controls how the data is read out, and how the data is processed by the microcomputer 138 when it is being read out.

Figure 7:
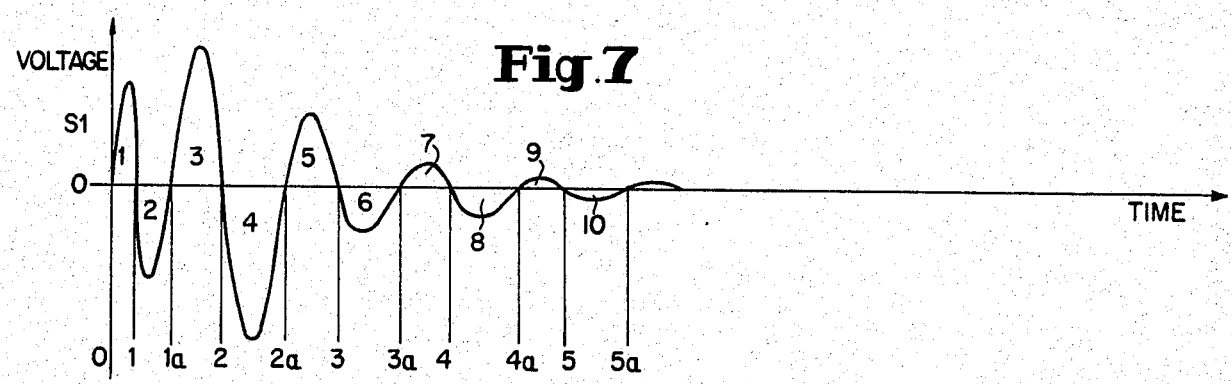
FIG. 7 is an input waveform of an electrical signal similar to that of FIG. 3a representing the heart sound.
Figure 8:
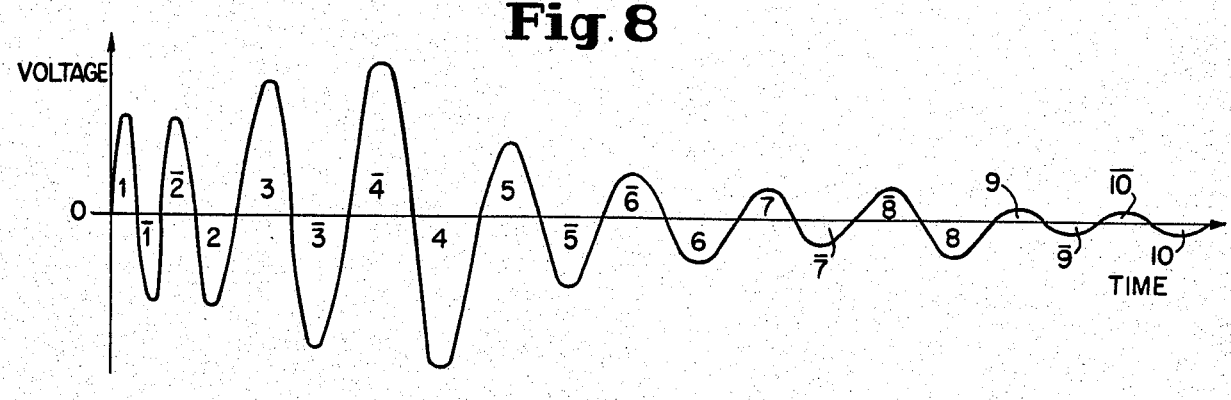
FIG. 8 is a waveform of the signal of FIG. 7 after it has been processed by the circuit of FIG. 6 when in the play one-half mode.

To facilitate better understanding of the operation reference is also made to FIGS. 7 and 8. The input waveform shown in FIG. 7 is composed of a series of cycles and when the signal passes through the A/D converter 134 the signal is sampled at a frequency of 2 kHz and the digital values of the voltage magnitudes are stored in the CMOS RAM 142. Each zero crossing of the signal, i.e. 1, 1a, 2, 2a, etc. is recorded as before, and the digital value nearest to zero is taken as the zero crossing. This information is also stored in the RAM 142.

Referring now to FIG. 8 when the data stored in the RAM 142 is being read out by the microcomputer 134, under the control of the program in the ROM 144, the digital values corresponding to the first positive wave cycle 1, between zero crossings 0 and 1 are read out. Then, the same digital values of the first positive half cycle are read out again until the zero crossing 1 but the microcomputer inverts these values to negative values. When these digital signals are converted back to analog signals as shown in FIG. 7 the first half cycle 1 is positive, then the first half cycle is repeated but inverted to be negative or complement waveform T. For the next half-cycle 2 the microcomputer 134 recognises that the digital data is negative and immediately inverts the data corresponding to this half cycle so that it is read out as positive 2 half cycle thus in the output signal there is a smooth transition from cycles 1 to T to 2, etc. The negative data of cycle 2 is then read out without inversion shown as cycle 2 in FIG. 8. This procedure is repeated for each half-cycle. If the digital values of the half-cycle are positive they are read out once positive and then read out negative to give the complement of the positive cycle. However, if the half-cycle values are negative they are first read out positive to give the complement waveform and are then read out negative. This technique results in a smooth transition between the adjacent cycles on the output waveform with the zero-crossings being used to determine proper execution of the algorithm stored in the ROM.

The effect of this procedure is that the sound quality appears to the trained listener to be more realistic or "musical" as it is generally called in the art. This procedure works by making use of the fact that the ear is insensitive to phase. In addition, special anomalies are not introduced within the range of hearing and consequently cross-over distinction is greatly reduced.

It should be appreciated that various modifications may be made to the embodiment without departing from the scope of the invention, the circuitry may be implemented in any current semiconductor technology such as CMOS, bipolar, NMOS or any other convenient technology. The invention can also be used in other applications, for example in mechanical vibration analysis, as a toy and for other acoustical monitoring purposes. The recording jack may be omitted from the structure as shown in FIG. 2 and the device can be applied to any repetitive sound, not only heart sounds or other physiologically originating sounds, and any number of repetitive cycles can be used, the 'slow down factor' being substantially proportional to the number of repetitive cycles. The sampling rate of the A/D converter need not be 1.5 KHz or 2 KHz but is preferably within the range 1-2.5 KHz. The storage capacity of the RAM is such that digital data corresponding to at least six seconds of original sound can be stored. In addition the CPU can use a datum other than zero to read out data corresponding to cycles of the input signal. Although the 6-pole low pass filter has a cut-off frequency of 600 Hz it should be understood that any other cut-off frequency which reduces the graininess of quantisation due to the signal processing will be acceptable.

Advantages of the embodiments are: conventional stethoscopes can easily be modified to accommodate the apparatus; the device is very simple and easy to implement; the processed sound is not perceived to change in pitch and is therefore recognisable by the physician who can then use this slowed-down sound to assist in interpretation of the signals and in formulating a clinical diagnosis, it uses readily available components and permits the user to readily compare the processed and unprocessed signals simply by using a switch. All in all, the embodiments disclose a device which mitigates the technical problems associated with the prior art devices, which is readily usuable by the physician, and which is clinically acceptable since it does not give a signal which is distorted and difficult for the physician to interpret.

I claim:

1. Sound processing and monitoring apparatus for processing an original sound and providing a sound output therefrom such that that sound output is recognizable as a slowed down version of the original sound at the same pitch, the apparatus comprising,
first sound transducer means for producing a cyclically varying analog input signal in response to an input sound;
analog to digital (A/D) converting means connected to said first sound transducer means for converting said analog input signal into a digital input signal;
memory means associated with said A/D converting means for storing said digital signal therein;
control means connected to said memory means for controlling the storage of said digital signal in said memory means, and for causing stored digital data corresponding to each respective analog input half-cycle to be read out of said memory means a predetermined multiple number of times to form a digital output signal;
said control means constituting means effective for controlling the phase of the output;
digital to analog (D/A) converting means for converting said digital output signal into an analog output signal, said analog output signal being composed of groups of said predetermined multiple number of half-cycles, each group corresponding to at least one half-cycle of said analog input signal; and
second sound transducer means connected to the output of said D/A converter for producing an output sound in response to said analog output signal, said output sound being recognizable as a slowed down version of said input sound with the same pitch.

2. Sound monitoring apparatus as claimed in claim 1, wherein each group corresponds to a full cycle of said analog input signal including means for varying the number of times digital data is read out from the memory means.

3. Sound monitoring apparatus as claimed in claim 2 wherein said control means is a microprocessor and said memory means is a random access memory.

4. Sound monitoring apparatus as claimed in claim 3 wherein the means for varying is a switch which is directly connected to said microprocessor, said means being manually adjustable.

5. Sound monitoring apparatus as claimed in claim 4 including low pass filter means connected between the sound transducer means and the A/D converter.

6. Sound monitoring apparatus as claimed in claim 4 wherein the memory capacity of the random access memory is such that digital data corresponding to at least six seconds can be stored therein.

7. Sound monitoring apparatus as claimed in claim 6 wherein the A/D converting means, memory means, microprocessor and D/A converting means are implemented by complementary-metaloxide semiconductor (CMOS) technology.

8. Sound monitoring apparatus as claimed in claim 1 wherein the control means counts the number of times said digital data crosses a reference value to determine when said digital data is read out from the memory.

9. Sound monitoring apparatus as claimed in claim 8 wherein the reference value is a zero voltage level.

10. Sound monitoring apparatus as claimed in claim 9 wherein said apparatus is incorporated into a stethoscope having a bell and binaural earpieces, said microphone means being located in proximity to the bell and said loudspeaker means being located in said stethoscope so as to transmit the sound in response to the analog output signal to the binaural earpieces.

11. Sound monitoring apparatus as claimed in claim 1 wherein the A/D and D/A connecting means are contained in the same physical device.

12. Sound monitoring apparatus as claimed in claim 1 wherein said control means splits data of a cycle into half cycles determined by the zero crossing, and causes data corresponding to a positive half cycle to be read out to give a positive output half cycle, then causes said data to be inverted and read out again to give a negative half cycle which is equivalent to the positive half cycle inverted about the zero axis, then causing data corresponding to a negative half cycle to be read out and inverted to give a positive half cycle then caused data corresponding to the negative half cycle to be read out again such that adjacent half cycles in said output signal are inverted about said zero axis such that the crossover between each adjacent pair of half cycles is substantially smooth.

13. Sound monitoring and processing apparatus as claimed in claim 1, wherein said control means constitutes means for controlling the polarity of the output cycles.

14. An electronic stethoscope for processing an original sound such that the sound output is recognizable as a slowed down version of the original sound at the same pitch, the stethescope comprising sound collection means for location at a source of sound, conduit means having an end connected to said collection means for collecting and transmitting an input sound, electronic signal processing means connected to the other end of the conduit means for receiving the transmitted sound, the received sound being formed by an input transducer into an input signal for said electronic processing means, bifurcated conduit means connected with an output of said electronic processing means, an earpiece means connected to each of the distal ends of said bifurcated conduit, said bifurcated conduit being adapted to receive electronically processed signals from said electronic signal processing means, said electronic signal processing means including analog to digital (A/D) converting means for converting an analog input signal into a digital signal, memory means associated with said analog to digital converting means for storing said digital signal therein control means associated with said memory means for reading out said stored digital data corresponding to each respective analog input cycle a predetermined multiple number of times, digital to analog converting means for providing an analog output signal corresponding to the digital data read out from said memory means, and sound transducer means for converting said analog output signal into an output sound, said output sound travelling along said bifurcated conduit to said earpiece means, and being recognizable as a slowed down version of the input sound with the same pitch.

15. An electronic stethoscope as claimed in claim 14 wherein said electronic processing means includes means for controlling the number of times said digital data is read out from the memory means.

16. An electronic stethoscope as claimed in claim 15 wherein means for varying the number of times said digital data is read out from said memory means is a switch directly connected to said control means and being manually operable.

17. An electronic stethoscope as claimed in claim 16 wherein said electronic processing means is located in a housing, said housing being connectable to said conduit means at one end and being connected to said bifurcated conduit at the other end, the switch being located on the housing and including a pointer and a scale to facilitate setting the number of times said digital data is to be read out from said memory means.

18. An electronic stethescope as claimed in claim 14 wherein said sound collection means is a bell.

19. In a stethescope having pickup bell means for location at a source of sound and for collecting sound emanating from said source to provide an input sound signal composed of cycles, conduit means having one end connected to the bell means and the other end bifurcating to form two separate conduit means, earpiece means located at the distal ends of said bifurcated conduit means, said conduit means guiding said sound collected by said bell means and transmitting it via said bifurcated conduit means to said earpiece means, the improvement comprising:

an electronic signal processing means in the acoustic pathway between said bell means and said earpiece means, in which the electronic signal processing means is mounted, and having a port connected to one end of said conduit means and another port connected to said bifurcated conduit means, said electronic signal processing means processing said input sound signal to provide an output sound signal, in which each respective input sound cycle is repeated a predetermined multiple number of times to form a set of cycles, said output signal being composed of successive sets of such cycles, said output sound signal being recognizable with the same pitch such that the pitch appears to be the same as the input sound signal but is reproduced at a slower rate, said slower rate being a function of the number of times each of said input signals is repeated.

20. A method of processing a cyclically varying input sound signal to produce an output sound signal which is recognizable as a slowed-down version of the input sound signal; comprising the steps of,
(a) converting said sound wave into a cyclically varying electrical analog input signal, each signal having a positive half-cycle and a negative half-cycle,
(b) converting said analog input signal into groups of digital data, each group corresponding to one half-cycle of the analog input signal,
(c) storing said groups of digital data in a memory means,
(d) in accordance with a signal from a controller, reading out a first group of digital data values corresponding to a first positive half-cycle and converting said group of digital data values to an analog first positive half-cycle output signal,
(e) again reading out said first group of digital data values corresponding to said first positive half-cycle and inverting said digital data values to negative values,
(f) converting said negative data values to an analog first negative half-cycle output signal,
(g) reading out a second group digital data values from the memory means corresponding to a first negative half-cycle being read out and inverting said negative data to positive data values, and converting said positive data values to a second positive half-cycle output signal,
(h) again reading out from the memory means said second group of data values corresponding to the first negative half-cycle and converting said negative data values to an analog second negative half-cycle output signal,
repeating the above steps (d)-(h) for successive groups of data values stored in the memory corresponding to stored half-cycles of the analog input signal,
converting said analog electrical output signals to an output sound signal, which is recognizable as a slowed down version of the input sound signal.

21. A method of processing a cyclically varying sound wave each cycle having positive and negative half cycles comprising the steps of,
converting the cyclically varying sound wave into an electrical analog input signal,
converting the electrical analog input signal into groups of digital data each group corresponding to one half cycle of the analog input signal,
storing said groups of data in memory means in accordance with the signal from a controller reading out each group of data at least three times,
when each group of data requires to be read out an even number of times from said memory means reading out data corresponding to each positive half cycle and inverting even numbered groups of data to give negative data values,
reading out data corresponding to each negative half cycle and inverting odd numbered groups of data to give positive data values,
converting said read out data values to an electrical analog output signal,
when each group of data requires to be read out an odd number of times from said memory means reading out data corresponding to each positive half cycle and inverting even numbered groups to give negative data values then reading out data corresponding to each negative half cycle and inverting even numbered groups of data to give positive data values, converting said read out data values to an electrical analog output signal, converting said electrical analog output signal to an output sound wave, the frequency of the output sound wave being at least three times the frequency of the input wave.

22. A method as claimed in claim 21 wherein the groups of data are read out from the memory means three to five times.

23. A method producing a slowed down sound wave from an original cyclically varying sound wave comprising the steps of:

converting the cyclically varying sound wave into a cyclically varying analog input signal, each signal having a positive half-cycle and a negative half-cycle, converting said half-cycle into respective groups of digital data, storing each group of said digital data groups in a memory in accordance with a signal from a controller, reading out each group of data from the memory successively at least three times, inverting the data of each alternate half-cycle data group each subsequent time it is read out, converting said read out data to an electrical analog output signal, converting said electrical analog output signal to an output sound signal which is recognizable as a slowed down version of the input sound signal with the same pitch.

24. A heart sound analyzer for processing an original sound such that that sound output is recognizable as a slowed down version of the original heart sound at the same pitch, the analyzer comprising, first sound transducer means for producing a cyclically varying analog input signal in response to an input heart sound;

analog to digital (A/D) converting means connected to said sound transducer means for converting said analog input signal into a digital input signal;

memory means associated with said A/D converting means for storing said digital input signal therein;

control means for controlling the storage of said digital input signal in said memory means, and for causing stored digital data corresponding to each respective analog input half-cycle to be read out of said memory means a predetermined multiple number of times to form a digital output signal;

said control means constituting means effective to split the data of a single cycle into half-cycle determined by a zero-crossing procedure, said control means causing data corresponding to a positive half-cycle to be read out successively to give a positive output half-cycle, then causing said data to be inverted and read out again to give a negative half-cycle which is equivalent to the positive half-cycle mirrored about the zero axis, said control means then causing data corresponding to a negative half-cycle to be read out, inverted to give a positive half-cycle and then causing said same data to be read out again corresponding to the negative half-cycle such that each half-cycle in said output signal is mirrored about said zero axis such that the crossover between each adjacent pair of half-cycles is substantially smooth.

25. A heart sound analyzer as claimed in claim 24 wherein said half-cycles are read out a predetermined number of times and adjacent half-cycles having opposite polarity and being read out such that the analog output signal is composed of cycles which are of laternate polarity and which have a substantially smooth transition from one half-cycle to the next when crossing the zero axis.

* * * * *